(12) United States Patent
Beals et al.

(10) Patent No.: US 8,541,426 B2
(45) Date of Patent: Sep. 24, 2013

(54) PHARMACEUTICAL COMPOSITIONS AND METHODS OF TREATING DRY EYE DISORDERS

(75) Inventors: Channing R. Beals, Westfield, NJ (US); Elizabeth WoldeMussie, Laguna Niguel, CA (US); Hovhannes John Gukasyan, San Diego, CA (US); Jingwen Ma, San Diego, CA (US)

(73) Assignee: Pfizer Inc., New York, NY (US)

( * ) Notice: Subject to any disclaimer, the term of this patent is extended or adjusted under 35 U.S.C. 154(b) by 544 days.

(21) Appl. No.: 12/668,604

(22) PCT Filed: Jul. 4, 2008

(86) PCT No.: PCT/IB2008/001819
§ 371 (c)(1), (2), (4) Date: Jun. 10, 2010

(87) PCT Pub. No.: WO2009/007839
PCT Pub. Date: Jan. 15, 2009

(65) Prior Publication Data
US 2010/0267751 A1    Oct. 21, 2010

Related U.S. Application Data

(60) Provisional application No. 60/949,216, filed on Jul. 11, 2007, provisional application No. 61/060,032, filed on Jun. 9, 2008.

(51) Int. Cl.
*A61K 31/519*    (2006.01)
(52) U.S. Cl.
USPC ........................................................ 514/265.1
(58) Field of Classification Search
None
See application file for complete search history.

(56) References Cited

U.S. PATENT DOCUMENTS

| | | | |
|---|---|---|---|
| 4,818,537 A | 4/1989 | Guo | |
| 4,966,773 A | 10/1990 | Gressel et al. | |
| 5,041,434 A | 8/1991 | Lubkin | |
| 5,290,572 A | 3/1994 | MacKeen | |
| 5,696,166 A | 12/1997 | Yanni et al. | |
| 5,800,807 A | 9/1998 | Hu et al. | |
| 5,968,912 A | 10/1999 | Ojo-Amaize | |
| 6,080,748 A * | 6/2000 | Uckun et al. | 424/178.1 |
| 6,153,607 A | 11/2000 | Pflugfelder et al. | |
| 6,627,754 B2 | 9/2003 | Blumenkopf et al. | |
| 7,091,208 B2 | 8/2006 | Blumenkopf et al. | |
| 2002/0111360 A1 | 8/2002 | Yiv et al. | |
| 2002/0132767 A1 | 9/2002 | Rosen et al. | |
| 2002/0165243 A1 | 11/2002 | Uckun et al. | |

FOREIGN PATENT DOCUMENTS

| | | |
|---|---|---|
| WO | WO 01/42246 | 6/2001 |
| WO | WO 02/096909 | 12/2002 |
| WO | WO 03/048162 | 6/2003 |
| WO | WO 2007/012953 | 2/2007 |
| WO | WO 2007/062459 | 6/2007 |
| WO | WO 2007/077949 | 7/2007 |
| WO | WO 2008/043019 | 4/2008 |

OTHER PUBLICATIONS

Clinical Trial NCT00147498 (Sep. 6, 2005).*

* cited by examiner

*Primary Examiner* — Craig Ricci
(74) *Attorney, Agent, or Firm* — Pfizer Inc.

(57) ABSTRACT

Inhibitors of Janus kinase-3 ("Jak3") are useful for treating dry eye disorders and other disorders requiring the wetting of the eye. Jak3 inhibitors useful for treating eye disorders include the compound 3-{(3R,4R)-4-Methyl-3-[methyl-(7H-pyrrolo [2,3-d]pyrimidin-4-yl)-amino]-piperidin-1-yl}-3-oxo-propionitrile.

10 Claims, 8 Drawing Sheets

PHARMACEUTICAL COMPOSITIONS AND METHODS OF TREATING DRY EYE DISORDERS

This application claims the benefit of U.S. Provisional Application No. 60/949,216 filed Jul. 11, 2007, and U.S. Provisional Application No. 61/060,032 filed Jun. 9, 2008, the contents of which are hereby incorporated by reference in their entireties.

BACKGROUND OF THE INVENTION

Dry eye, also known generically as keratoconjunctivitis sicca, is a common opthalmological disorder affecting millions of Americans each year. Dry eye is a multifactorial disease of the tears and ocular surface that results in symptoms of discomfort, visual disturbance, and tear film instability with potential damage to the ocular surface. It is accompanied by increased osmolarity of the tear film and inflammation of the ocular surface.

Dry eye may afflict an individual with varying severity. Dry eye is particularly widespread among post-menopausal women due to hormonal changes following the cessation of fertility. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

The etiopathogenic classification of dry eye was first developed in 1995 by the National Eye Institute/Industry Dry Eye Workshop and was further updated in the January 2007 definition. *The Ocular Surface*, vol. 5, no. 2, 75-92 (2007). The major classes of dry eye include aqueous tear-deficient dry eye and evaporative dry eye. Aqueous tear-deficient dry eye comprises two major subclasses, Sjogren syndrome dry eye and non-Sjogren syndrome dry eye (primary and secondary lacrimal gland deficiencies, obstruction of the lacrimal gland ducts, reflex hyposecretion, reflex motor block). Evaporative dry eye, resulting from excessive water loss from the exposed ocular surface in the presence of normal lacrimal secretory function, comprises the subclasses of intrinsic causes (meibomian gland dysfunction, lid aperture and lid/globe disorders, low blink rate) and extrinsic causes (ocular surface disorders and disease, contact lens wear, allergic conjunctivitis such as vernal keratoconjunctivitis).

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the national Eye Institute/Industry workshop on Clinical Trials in Dry Eyes, the CLAO Journal*, vol. 21, no. 4, pp 221-231 (1995).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g. McCulley and Shine, *Tear film structure and dry eye, Contactologio*, vol. 20(4), pp 145-9 (1998). Phosphilipid drug delivery systems involving phospholipids, propellants and an active substance are also known, see U.S. Pat. No. 5,174,988.

Another approach involves the provision of lubricating substances in lieu of artificial tears. For example, U.S. Pat. No. 4,818,537 (Guo) discloses the use of a lubricating liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids such as conjugated estrogens to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Some literature reports suggest that patients suffering from dry eye syndrome disproportionately exhibit the hallmarks of excessive inflammation in relevant ocular tissues, such as the lacrimal and meibomian glands. The use of various compounds to treat dry eye patients, such as steroids e.g. U.S. Pat. No. 5,968,912; Marsh, et al., Topical nonpreserved methylprednisolone therapy for keratoconjunctivitis sicca in Sjogren syndrome, Opthalmology, 106(5): 881-816 (1999); Plugfelder et al, U.S. Pat. No. 6,153,607]; cytokine release inhibitors (Yanni, J. M.; et al WO0003705 A1), cyclosporine A [Tauber, *J. Adv. Exp. Med. Biol.* 1998, 438, (Lacrimal Gland, Tear From and Dry Eye Syndromes 2), 969] and 15-HETE (Yanni et al., U.S. Pat. No. 5,696,166) has been disclosed.

In addition to dry eye, Jak3 inhibitors may be useful in the treatment of other inflammation-linked ocular disorders, including but not limited to glaucoma, uveitis, diabetic retinopathy and age-related macular degeneration. A CNIB-funded study found that patients having the inflammatory biomarker, anticardiolipin, were four times more likely to progress in glaucoma. Jak3 inhibitors have previously been suggested for the treatment of diabetes, although there appears no suggestion for diabetic retinopathy in particular. Cetkovic-Cvrle, M. and Uckun, F. M., *Arch Immunol Ther Exp (Warsz)*, 52(2), 69-82 (2004). Rodrigues found that the isolation of immunoglobulins, complement proteins, cytokines and activated microglia, in retinal pigment epithelium (RPE) cells and drusen provided evidence for the role of inflammation in dry age-related macular degeneration. Rodrigues E. B., *Opthalmologica*, 221(3)143-52 (2007).

SUMMARY OF THE INVENTION

The present invention is directed to a method for the treatment of dry eye which comprises administering to a mammal a composition comprising a pharmaceutically acceptable carrier and a pharmaceutically effective amount of a Janus kinase-3 ("Jak3") inhibitor. In one aspect, the Jak3 inhibitors have the compound of formula I:

I wherein
$R^1$ is a group of the formula wherein y is 0, 1 or 2;
$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$-amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$-amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^5$ is $(C_2-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$-amino$(C_1-C_6)$acyl, $R^{15}R^{16}N$—CO—O—, $R^{15}R^{16}N$—CO—$(C_1-C_6)$alkyl, $(C_1-C_6)$alkyl-S(O)$_m$, $R^{15}R^{16}NS(O)_m$, $R^{15}R^{16}NS(O)_m$ $(C_1-C_6)$alkyl, $R^{15}S(O)_m R^{16}N$, $R^{15}S(O)_m R^{16}N(C_1-C_6)$alkyl wherein m is 0, 1 or 2 and $R^{15}$ and $R^{16}$ are each independently selected from hydrogen or $(C_1-C_6)$alkyl; or a group of the formula

II wherein a is 0, 1, 2, 3 or 4;
b, c, e, f and g are each independently 0 or 1;
d is 0, 1, 2, or 3;

X is $S(O)_n$ wherein n is 0, 1 or 2; oxygen, carbonyl or —C(=N-cyano)-;
Y is $S(O)_n$ wherein n is 0, 1 or 2; or carbonyl; and
Z is carbonyl, C(O)O—, C(O)NR— or $S(O)_n$ wherein n is 0, 1 or 2;
$R^6, R^7, R^8, R^9, R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$ amino, cyano, cyano$(C_1-C_6)$alkyl, trifluoromethyl$(C_1-C_6)$alkyl, nitro, nitro$(C_1-C_6)$alkyl or $(C_1-C_6)$acylamino;
$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$ amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$-amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-S(O)$_m$, $(C_1-C_6)$alkyl-S(O)$_m$—$(C_1-C_6)$alkyl, $R^{15}R^{16}NS(O)_m$, $R^{15}R^{16}NS(O)_m$ $(C_1-C_6)$alkyl, $R^{15}S(O)_m$ $R^{16}N$, $R^{15}S(O)_m R^{16}N(C_1-C_6)$alkyl wherein m is 0, 1 or 2 and $R^{15}$ and $R^{16}$ are each independently selected from hydrogen or $(C_1-C_6)$alkyl;
$R^2$ and $R^3$ are each independently selected from the group consisting of hydrogen, deuterium, amino, halo, hydroxy, nitro, carboxy, $(C_2-C_6)$alkenyl, $(C_2-C_6)$alkynyl, trifluoromethyl, trifluoromethoxy, $(C_1-C_6)$alkyl, $(C_1-C_6)$alkoxy, $(C_3-C_{10})$cycloalkyl wherein the alkyl, alkoxy or cycloalkyl groups are optionally substituted by one to three groups selected from halo, hydroxy, carboxy, amino $(C_1-C_6)$alkylthio, $(C_1-C_6)$alkylamino, $((C_1-C_6)$alkyl$)_2$-amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$-amino, $(C_6-C_{10})$arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkylamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl$)_2$-amino, $(C_1-C_6)$alkylamino$(C_1-C_6)$alkyl, $((C_1-C_6)$alkyl$)_2$-amino$(C_1-C_6)$alkyl, hydroxy, $(C_1-C_6)$alkoxy, carboxy, carboxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocycloalkyl, amino-CO—NH—, $(C_1-C_6)$alkylamino-CO—NH—, $((C_1-C_6)$alkyl$)_2$-amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl$)_2$-amino-CO—NH—$(C_1-C_6)$alkyl, $(C_6-C_{10})$ arylamino-CO—NH—($C_1$-$C_6$)alkyl, ($C_5$-$C_9$)heteroarylamino-CO—NH—($C_1$-$C_6$)alkyl, ($C_1$-$C_6$)alkylsulfonyl, ($C_1$-$C_6$)alkylsulfonylamino, ($C_1$-$C_6$)alkylsulfonylamino($C_1$-$C_6$)alkyl, ($C_6$-$C_{10}$)arylsulfonyl, ($C_6$-$C_{10}$)arylsulfonylamino, ($C_6$-$C_{10}$)arylsulfonylamino($C_1$-$C_6$)alkyl, ($C_1$-$C_6$)alkylsulfonylamino, ($C_1$-$C_6$)alkylsulfonylamino($C_1$-$C_6$)alkyl, ($C_5$-$C_9$)heteroaryl or ($C_2$-$C_9$)heterocycloalkyl, or the pharmaceutically acceptable salts thereof.

The present invention is also directed to a method for the treatment of glaucoma, uveitis, diabetic retinopathy and age-related macular degeneration comprising administering to a mammal a composition comprising a pharmaceutically effective amount of a Jak3 inhibitor having the compound of formula I.

Specific compounds of formula I include those wherein said compound is selected from the group consisting of:
Methyl-[4-methyl-1-(propane-1-sulfonyl)-piperidin-3-yl]-(7H-pyrrolo[2,3-d]pyrimidin-4-yl)-amine;
4-Methyl-3-[methyl-(7H-pyrrolo[2,3-d]pyrimidin-4-yl)-amino]-piperidine-1-carboxylic acid methyl ester;
3,3,3-Trifluoro-1-{4-methyl-3-[methyl-(7H-pyrrolo[2,3-d]pyrimidin-4-yl)-amino]-piperidin-1-yl}-propan-1-one;
4-Methyl-3-[methyl-(7H-pyrrolo[2,3-d]pyrimidin-4-yl)-amino]-piperidine-1-carboxylic acid dimethylamide;
({4-Methyl-3-[methyl-(7H-pyrrolo[2,3-d]pyrimidin-4-yl)-amino]-piperidine-1-carbonyl}-amino)-acetic acid ethyl ester;
3-{4-Methyl-3-[methyl-(7H-pyrrolo[2,3-d]pyrimidin-4-yl)-amino]-piperidin-1-yl}-3-oxo-propionitrile;
3,3,3-Trifluoro-1-{4-methyl-3-[methyl-(5-methyl-7H-pyrrolo[2,3-d]pyrimidin-4-yl)-amino]-piperidin-1-yl}-propan-1-one;
1-{4-Methyl-3-[methyl-(7H-pyrrolo[2,3-d]pyrimidin-4-yl)-amino]-piperidin-1-yl}-but-3-yn-1-one;
1-{3-[(5-Chloro-7H-pyrrolo[2,3-d]pyrimidin-4-yl)-methyl-amino]-4-methyl-piperidin-1-yl}-propan-1-one;
1-{3-[(5-Fluoro-7H-pyrrolo[2,3-d]pyrimidin-4-yl)-methyl-amino]-4-methyl-piperidin-1-yl}-propan-1-one;
N-cyano-4-methyl-3-[methyl-(7H-pyrrolo[2,3-d]pyrimidin-4-yl)-amino]-N'-propyl-piperidine-1-carboxamidine; and
N-cyano-4,N',N'-Trimethyl-3-[methyl-(7H-pyrrolo[2,3-d]pyrimidin-4-yl)-amino]-piperidine-1-carboxamidine.

In a particular embodiment, the Jak3 inhibitor is 3-{(3R,4R)-4-Methyl-3-[methyl-(7H-pyrrolo[2,3-d]pyrimidin-4-yl)-amino]-piperidin-1-yl}-3-oxo-propionitrile (CP0690550), which has the structure:

In one aspect of the invention, administration of the Jak3 inhibitor significantly increases tear production volume as compared to untreated tear production volume within two days. In a further aspect of the invention, administration of the Jak3 inhibitor increases tear production volume by at least 30% over initial tear production within the first two days of administration. In a further aspect, administration of the Jak3 inhibitor increases tear production volume by at least 50% over initial tear production within the first two days of administration. In a further aspect of the invention, administration of the Jak3 inhibitor increases tear production volume by at least 100% over initial tear volume within the first two days of administration. In another embodiment, the Jak3 inhibitor increases tear production volume to a level comparable to that of normal tear production. In a further aspect of this embodiment, the Jak3 inhibitor increases tear production volume to a level comparable to that of normal tear production within 8 days of initial treatment.

In an alternative embodiment, the invention comprises restoration of normal tear production in a mammal comprising administering to a mammal a composition comprising a pharmaceutically acceptable carrier and a pharmaceutically effective amount of a Janus kinase-3 ("Jak3") inhibitor. In one aspect of this embodiment, the JAK3 inhibitor is 3-{(3R,4R)-4-Methyl-3-[methyl-(7H-pyrrolo[2,3-d]pyrimidin-4-yl)-amino]-piperidin-1-yl}-3-oxo-propionitrile (CP0690550).

In another aspect of the invention, the Jak3 inhibitor is administered at most twice a day (BID). In a further aspect, the Jak 3 inhibitor is administered daily (QD).

In a further aspect of the invention, the composition is topically administered to the eye.

In another aspect of the invention, the pharmaceutically effective amount of the Jak3 inhibitor is 0.0001% to less than 1.0% (w/w). In a further aspect the amount of the Jak3 inhibitor is 0.0003% to less than 0.1% (w/w). In another aspect of the invention, the amount of the Jak3 inhibitor is 0.0003 to 0.03% (w/w). In still another aspect the amount of the Jak3 inhibitor is 0.003% to 0.005% (w/w). In still another aspect, the amount of the Jak3 inhibitor is 0.01% to 0.03% (w/w). In a still further embodiment, the amount of Jak3 inhibitor is about 0.003%, 0.005%, 0.01% or 0.03% (w/w).

In another aspect of the invention, the topical ophthalmic composition further comprises a tonicity agent and a buffer. In a still another aspect of the invention, the tonicity agent is either a simple sugar or a sugar alcohol. In still another aspect of the invention, the buffer is selected from phosphate or citrate.

In still another aspect of the invention, the composition further comprises a surfactant. In a preferred embodiment of the invention, the surfactant is selected from TritonX114 and tyloxapol. In further aspect of this embodiment, the composition further comprises a stabilizing polymer. In a still further aspect of the invention, the stabilizing polymer is carbomer 974p.

DETAILED DESCRIPTION OF THE INVENTION

According to the present invention, inhibitors of Janus kinase-3 (Jak3), are administered to a mammal suffering from dry eye, and in particular, to a human patient suffering from dry eye. The Jak3 selective inhibitors of the present invention in one aspect have selectivity for inhibition of Jak3 relative to other protein tyrosine kinases, particularly the closely related family member, Jak2. This is because Jak2 controls signaling through the erythropoietin (EPO), macrophage colony-stimulating factor (M-CSF), granulocyte-macrophage (GM)_CSF, and thrombopoietin (TPO) receptors. Moreover Jak2 deficiency is embryonically lethal due to impaired erythropoiesis. Significant pharmacologic inhibition of Jak2 in vivo could be expected to result in anemia, thrombocytopenia, and leukopenia. Pesu et al, Immunological Reviews 203, 127-142 (2005). At the enzymatic level, the Jak3 inhibitors of the present invention are at least 10 fold more potent against Jak3 versus Jak2, and are greater than 3000-fold specific relative to other kinases.

The present invention relates to a method of treating dry eye comprising administering to a mammal a composition comprising a pharmaceutically acceptable carrier and a pharmaceutically effective amount of a Janus kinase-3 ("Jak3") inhibitor having the formula I and/or the specific embodiments as described above. Jak3 inhibitors are disclosed in U.S. Pat. Nos. 6,627,754 and 7,091,208, the contents of which are incorporated by reference herein. A particular embodiment of the invention comprises administering to a patient a pharmaceutically effective amount of 3-{(3R,4R)-4-Methyl-3-[methyl-(7H-pyrrolo[2,3-d]pyrimidin-4-yl)-amino]-piperidin-1-yl}-3-oxo-propionitrile.

The term "alkyl", as used herein, unless otherwise indicated, includes saturated monovalent hydrocarbon radicals having straight or branched moieties or combinations thereof.

The term "alkoxy", as used herein, includes O-alkyl groups wherein "alkyl" is defined above.

The term "halo", as used herein, unless otherwise indicated, includes fluoro, chloro, bromo or iodo.

The compounds of this invention may contain double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

($C_2$-$C_9$)Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said ($C_2$-$C_9$)heterocycloalkyl rings is through a carbon or a $sp^3$ hybridized nitrogen heteroatom.

($C_2$-$C_9$)Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said ($C_2$-$C_9$)heterocycloalkyl rings is through a carbon atom or a $sp^3$ hybridized nitrogen heteroatom.

($C_6$-$C_{10}$)aryl when used herein refers to phenyl or naphthyl.

Preferred compounds of formula I include those wherein a is 0; b is 1; X is carbonyl; c is 0; d is 0; e is 0; f is 0; and g is 0. Additional preferred compounds of formula I include those wherein a is 0; b is 1; X is carbonyl; c is 0; d is 1; e is 0; f is 0, and g is 0. Additional preferred compounds of formula I include those wherein a is 0; b is 1; X is carbonyl; c is 1; d is 0; e is 0; f is 0; and g is 0. Additional preferred compounds of formula I include those wherein a is 0; b is 1; X is —C(=N=cyano)-; c is 1; d is 0; e is 0; f is 0; and g is 0.

Additional preferred compounds of formula I include those wherein a is 0; b is 0; c is 0; d is 0; e is 0; f is 0; g is 1; and Z is —C(O)—O—. Additional preferred compounds of formula I include those wherein a is 0; b is 1; X is $S(O)_n$; n is 2; c is 0; d is 0; e is 0; f is 0; and g is 0. Additional preferred compounds of formula I include those wherein a is 0; b is 1; X is $S(O)_n$; n is 2; c is 0; d is 2; e is 0; f is 1; g is 1; and Z is carbonyl. Additional preferred compounds of formula I include those wherein a is 0; b is 1; X is $S(O)_n$; n is 2; c is 0; d is 2; e is 0; f is 1; and g is 0. Additional preferred compounds of formula I include those wherein a is 0; b is 1; X is carbonyl; c is 1; d is 0; e is 1; Y is $S(O)_n$; n is 2; f is 0; and g is 0. Additional preferred compounds of formula I include those wherein a is 0; b is 1; X is $S(O)_n$; n is 2; c is 1; d is 0; e is 0; f is 0; and g is 0. Additional preferred compounds of formula I include those wherein a is 1; b is 1; X is carbonyl; c is 1; d is 0; e is 0; f is 0; and g is 0. Additional preferred compounds of formula I include those wherein a is 0; b is 1; X is $S(O)_n$; c is 0; d is 1; e is 1; Y is $S(O)_n$; n is 2; f is 0; and g is 0. Additional preferred compounds of formula I include those wherein a is 0; b is 1; X is $S(O)_n$; c is 0; d is 1; e is 1; Y is $S(O)_n$; n is 2; f is 1; and g is 0. Additional preferred compounds of formula I include those wherein a is 0; b is 1; X is oxygen; c is 0; d is 1; e is 1; Y is $S(O)_n$; n is 2; f is 1; and g is 0. Additional preferred compounds of formula I include those wherein a is 0; b is 1; X is oxygen; c is 0; d is 1; e is 1; Y is $S(O)_n$; n is 2; f is 0; and g is 0. Additional preferred compounds of formula I include those wherein a is 0; b is 1; X is carbonyl; c is 1; d is 1; e is 1; Y is $S(O)_n$; f is 0; and g is 0. Additional preferred compounds of formula I include those wherein a is 0; b is 1; X is carbonyl;

c is 1; d is 1; e is 1; Y is $S(O)_n$; n is 2; f is 1; and g is 0. Additional preferred compounds of formula I include those wherein $R^{12}$ is cyano, trifluoromethyl, $(C_1-C_6)$alkyl, trifluoromethyl$(C_1-C_6)$alkyl, $(C_1-C_6)$alkylamino, $((C_1-C_6)$alkyl$)_2$-amino, $(C_2-C_6)$alkynyl, cyano$(C_1-C_6)$alkyl, $(C_1-C_6)$alkyl-S$(O)_m$ wherein m is 0, 1 or 2.

The compositions administered according to the present invention comprise a pharmaceutically effective amount of one or more of the specified Jak3 inhibitors. As used herein, a "pharmaceutically effective amount" is one which is sufficient to reduce or eliminate signs of symptoms of dry eye or other disorders requiring the wetting of the eye. An effective dosage can be administered in one or more administrations.

As is understood in the clinical context, administration of an effective amount of a drug, compound, or pharmaceutical composition may or may not be achieved in conjunction with another drug, compound, or pharmaceutical composition. Thus, an "effective amount" or "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, reducing and/or eliminating signs of symptoms of dry eye or other disorders requiring the wetting of the eye.

Most clinicians diagnose and treat Dry Eye Syndrome based on the symptoms alone (JAMA 2001; 286:2114-9). Responses to the McMonnies & Ho Dry Eye Questionnaire can be used as a tool to assess the symptoms of dry eye (score of more than 14.5 is consistent with dry eye diagnosis). Nonetheless, the National Eye Institute workshop on dry eyes defines 'symptoms of ocular discomfort' as only one aspect of 'dry eyes'. An analysis of demonstrable tear deficiency or possibility of excessive tear evaporation and damage to the exposed surface of the eye, can provide confirmation of a 'dry eye' diagnosis.

As used herein, "significantly increases tear production" means a statistically significant (i.e. $p<0.05$) increase in tear production as measured by standard ophthalmic practice, i.e. Schirmer's or phenol red threat test, fluorescein breakup time, or any of the tests described below.

The most common tests for dry eye are tear film break-up time, Schirmer test and fluorescein staining, although these tests are non-exhaustive. The following are known tests for dry eye and the cutoff value at which they are considered abnormal and indicative of dry eyes:

TABLE 1

| TEST | Abnormal cutoff value for dry eye diagnosis |
|---|---|
| Schirmer's I | Less than or equal to 5 mm wetting over 5 min |
| Phenol Red Thread | Less than 9 mm |
| Tear Breakup time | Less than or equal to 10 seconds |
| Fluorescein staining | More than 3 out of 15 |
| Rose Bengal staining | More than 3 out of 18 |
| Tear film osmolarity | Less than or equal to 312 mOsm/L |
| Impression cytology | More than 1 |
| Brush cytology | More than 1 |
| Tear lactoferrin | Less than or equal to 0.9 ug/mL |

Schirmer's I Test

In the Schirmer I test, the quantity of tears that are produced by the eye are measured: the tears are collected for approximately 5 minutes or so, to allow the ophthalmologist to determine whether the amount produced is sufficient for maintaining eye health or not. If not much tears are produced, then a tear deficient dry eye can be diagnosed. If enough tears are produced, but the patient still has symptoms of ocular discomfort, then evaporative dry eye may be diagnosed.

In the Schirmer I test, a 35 mm×5 mm size filter paper strip is used to measure the amount of tears that are produced over a period of 5 minutes. The strip is placed at the junction of the middle and lateral thirds of the lower eye lid under ambient light. The patient is instructed to look forward and to blink normally during the course of the test. A negative test (more than 10 mm wetting of the filter paper in 5 minutes) means that the patient produces a normal quantity of tears. Patients with dry eyes have wetting values of less than 5 mm in 5 minutes.

An important limitation of Schirmer test is that there may be considerable variability in the results of tests done at different times and by different doctors. Its main utility may really be in diagnosing patients with severe dry eyes.

There is some debate about the Schirmer I test. When an anesthetic eyedrop is NOT used then this test is thought to measure basal and reflex tear secretion. When an anesthetic eyedrop IS used then this test is thought to measure only the basic tear secretion. There is compelling reason to believe that the tears measured by these two different methods may not sufficiently differentiate between basic and reflex tear production. Most clinicians perform this test after using anesthetic eyedrops to numb the eye. However, The National Eye Institute workshop on dry eyes recommended not to use anesthetic eyedrops before performing this test. The cutoff value is similar whether or not anesthetic is used. To measure the reflex tear secretion Schirmer II test may be performed. Schirmer II test is performed by irritating the nasal mucosa with a cotton-tipped applicator prior to measuring tear production.

As an alternative to the Schirmer I or II test, which some clinicians consider unduly invasive and of little value for mild to moderate dry eyes, the phenol red thread test (Quick Zone®) can be used. A cotton thread impregnated with phenol red dye is used. Phenol red is pH sensitive and changes from yellow to red when wetted by tears. The crimped end of a 70 mm long thread is placed in the lower conjunctival formix. After 15 seconds, the length of the color change on the thread—indicating the length of the thread wetted by the tears is measured in millimeters. Wetting lengths should normally be between 9 mm and 20 mm. Patients with dry eyes have wetting values of less than 9 mm.

Tear Breakup Time (BUT)

In patients with dry eyes the tear film is unstable, and breaks up faster. Therefore the tear break up time in patients who have dry eyes is shorter. Fluorescein BreakUp Time (FBUT) is used most commonly. A strip of fluorescein is applied in the lower eyelid fornix and then removed. The patient is asked to blink three times and then look straight forward, without blinking. The tear film is observed under cobalt-blue filtered light of the slitlamp microscope and the time that elapsed between the last blink and appearance of the first break in the tear film is recorded with a stopwatch (a break is seen as a dark spot in a sea of blue). Fluorescein BUT of less than 10 seconds or less is consistent with dry eyes.

To overcome limitations caused by the potential invasiveness of the FBUT test, Non Invasive Break up time (NIBUT) methods have been developed. They are called Non Invasive because the eye is not touched. Instruments such as a keratometer, hand-held keratoscope or Tearscope are required to measure NIBUT. A prerupture phase that precedes actual break up of the tear film can also be observed with some techniques. This pre-rupture phase is termed Tear Thinning Time (TTT). Measurement is achieved by observing the distortion (TTT) and/or break up (NIBUT) of a keratometer mire (the reflected image of keratometer grid). The clinician focuses and views the crisp mires, and then records the time taken for the mire image to distort (TTT) and/or break up (NIBUT). NIBUT measurements are longer than fluorescein break up time. NIBUT values of less than 15 seconds are consistent with dry eyes. TTT/NIBUT are considered to be more patient-friendly, repeatable and precise.

As used herein, administration "in conjunction" includes simultaneous administration and/or administration at different times. Administration in conjunction also encompasses administration as a co-formulation or administration as separate compositions. As used herein, administration in conjunction is meant to encompass any circumstance wherein a Jak3 inhibitor and another agent are administered to an indivisual, which can occur simultaneously and/or separately. As further discussed herein, it is understood that a Jak3 inhibitor and the other agent can be administered at different dosing frequencies or intervals. For example, the Jak3 inhibitor can be administered daily, while the other agent can be administered less frequently. It is understood that the Jak3 inhibitor and the other agent can be administered using the same route of administration or different routes of administration.

An "individual" (alternatively referred to as a "subject") is a mammal, more preferably a human. A "mammal" includes, but is not limited to, farm animals (such as cows), sport animals, pets (such as cats, dogs, horses), primates, mice and rats.

The term "restoration of normal tear production" refers to the cessation of dry eye symptoms as described in standard ophthalmic practice, such as a response score of less than 14.5 in McMonnies & Ho Dry Eye Questionnaire and/or test results (i.e. from Schirmer's, red phenol, fluorescein etc as described in Table 1) which are in the normal variable range.

According to the methods of the present invention, a composition comprising one or more of the specified Jak3 inhibitors and a pharmaceutically acceptable carrier for topical ophthalmic administration or implantation into the conjunctival sac or anterior chamber of the eye is administered to a mammal in need thereof. The compositions are formulated in accordance with methods known in the art for the particular route of administration desired.

Generally, for compositions intended to be administered topically to the eye in the form of eye drops or eye ointments, the total amount of the Jak3 inhibitor will be about 0.0001 to less than 1.0% (w/w). A preferred range of the amount of the Jak3 inhibitor is 0.0003% to less than 0.1% (w/w), while an even more preferred range of the amount of the Jak3 inhibitor is 0.003 to 0.03% (w/w). Another preferred range of the amount of Jak3 inhibitor is 0.005% to 0.05% (w/w), and a still more preferred range is 0.01% to 0.03% (w/w).

Preferably, the compositions administered according to the present invention will be formulated as solutions, suspensions, emulsions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for Jak3 inhibitors which are sparingly soluble in water.

The compositions administered according to the present invention may also include various other ingredients, including but not limited to tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomalt, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general the tonicity agents of the invention will be present in the range of 2 to 4% w/w. Preferred tonicity agents of the invention include the simple sugars or the sugar alcohols. A particular embodiment of the invention is D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilize the inhibitor and stabilize colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet", approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more of the specific Jak3 inhibitors. Examples or artificial tears compositions useful as artificial tears carriers include, but are not limited to, commercial products, such as Visine Pure Tears®, Visine Tears Natural Tears Formula® (Johnson & Johnson) Tears Naturale®, Tears Naturale II®, Tears Naturale Free®, Bion Tears® (Alcon Laboratories, Inc. Forth Worth, Tex.), Refresh Tears®, Refresh Endura®, Refresh Plus® (Allergan Inc.). Examples of phospholipid carrier formulations include those disclosed in U.S. Pat. Nos. 4,804,539

(Guo et al.), 4,883,658 (Holly), 4,914,088 (glonek), 5,075,104 (Gressel et al.), 5,278,151 (Korb et al.), 5,294,607 (Glonek et al.), 5,371,108 (Korb et al.), 5,578,586 (Glonek et al.); the foregoing patents are incorporated herein by reference to the extent they disclose phospholipid compositions useful as phospholipid carriers of the present invention.

Palliative compounds designed to lubricate, "wet," approximate the consistency of endogenous tears, aid in natural tear build-up, or otherwise provide temporary relief of dry eye symptoms and conditions upon ocular administration of the eye are known in the art. Such palliative agents may, in some cases, serve a dual function as a tonicity agent, such as the monomeric polyols (glycerol, propylene glycol, ethylene glycol). The palliative compounds may enhance the viscosity of the composition, and include, but are not limited to: monomeric polyols, polymeric polyols, such as polyethylene glycol, hydroxypropylmethyl cellulose ("HPMC"), carboxy methylcellulose sodium, hydroxyl propylcellulose ("HPC"), dextrans, such as dextran 70; water soluble proteins, such as gelatin; and vinyl polymers, such as polyvinyl alcohol, polyvinylpyrrolidinone, povidone, and carbomers, such as, carbomer 941, carbomer 940, carbomer 971P, carbomer 974P.

Additional agents that may be added to the ophthalmic compositions of the present invention are demulcents which function as a stabilizing polymer. The stabilizing polymer should be an ionic/charged example with precedence for topical ocular use, more specifically a polymer that carries negative charge on it's surface that can exhibit a zeta-potential of (−)10-50 mV for physical stability and capable of making a dispersion in water (i.e. water soluble). A preferred stabilizing polymer of the invention would be polyelectrolyte or polyectrolytes if more than one, from the family of cross-linked polyacrylates, such as carbomers and Pemulen®, specifically Carbomer 974p (polyacrylic acid), at 0.1-0.5% w/w. As noted above, the carbomers may also function as a palliative compound.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps").

Topical ophthalmic products are typically packaged in multidose form. Preservative are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquarternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The preferred compositions of the present invention are intended for administration to a human patient suffering from dry eye or symptoms of dry eye. Preferably, such compositions will be administered topically. In general, the doses used for the above described purposes will bary but will be in an effective amount to eliminate or improve dry eye conditions. Generally, 1-2 drops of such compositions will be administered from once to many times per day. Preferably such compositions will be administered once (QD) or twice (BID) daily.

Representative eye drop formulations are provided in Example 2 below.

Example 1

1-{4-Methyl-3-[methyl-(7H-pyrrolo[2,3-d]pyrimidin-4-yl)-amino]-piperidin-1-yl}-ethanone and 3-{(3R,4R)-4-Methyl-3-[methyl-(7H-pyrrolo[2,3-d]pyrimidin-4-yl)-amino]-piperidin-1-yl}-3-oxo-propionitrile Method A:
(1-Benzyl-4-methyl-piperidin-3-yl)-methyl-amine To a stirred solution of 1-benzyl-4-methyl-piperidin-3-one (2.3 grams, 11.5 mmol), prepared by the methods of Iorio, M. A. and Damia, G., Tetrahedron, 26, 5519 (1970) and Grieco et al., Journal of the American Chemical Society, 107, 1768 (1985), (modified using 5% methanol as a co-solvent), both references are incorporated by reference in their entirety, dissolved in 23 mL of 2 M methylamine in tetrahydrofuran was added 1.4 mL (23 mmol) of acetic acid and the resulting mixture stirred in a sealed tube for 16 hours at room temperature. Triacetoxy sodium borohydride (4.9 grams, 23 mmol) was added and the new mixture stirred at room temperature in a sealed tube for 24 h, at which time, the reaction was quenched upon addition of 1 N sodium hydroxide (50 mL). The reaction mixture was then extracted 3×80 mL with ether, the combined ether layers dried over sodium sulfate ($Na_2SO_4$) and concentrated to dryness in vacuo affording 1.7 grams (69%) of the title compound as a white solid. LRMS: 219.1 (M+1).

Method B: (1-Benzyl-4-methyl-piperidin-3-yl)-methyl-(7H-pyrrolo[2,3-d]pyrimidin-4-yl)-amine A solution of 4-chloropyrrolo[2,3-d]pyrimidine (2.4 grams, 15.9 mmol), prepared by the method of Davoll, J. Am. Chem. Soc., 82, 131 (1960), which is incorporated by reference in its entirety, and the product from Method A (1.7 grams, 7.95 mmol) dissolved in 2 equivalents of triethylamine was heated in a sealed tube at 100° C. for 3 days. Following cooling to room temperature and concentration under reduced pressure, the residue was purified by flash chromatography (silica; 3% methanol in dichloromethane) affording 1.3 grams (50%) of the title compound as a colorless oil. LRMS: 336.1 (M+1).

Method C: Methyl-(4-methyl-piperidin-3-yl)-(7H-pyrrolo[2,3-d]pyrimidin-4-yl)-amine To the product from Method B (0.7 grams, 2.19 mmol) dissolved in 15 mL of ethanol was added 1.5 mL of 2 N hydrochloric acid and the reaction mixture degassed by nitrogen purge. To the reaction mixture was then added 0.5 grams of 20% palladium hydroxide on carbon (50% water) (Aldrich) and the resulting mixture shaken (Parr-Shaker) under a 50 psi atmosphere of hydrogen at room temperature for 2 days. The Celite filtered reaction mixture was concentrated to dryness in vacuo and the residue purified by flash chromatography (silica; 5% methanol in dichloromethane) affording 0.48 grams (90%) of the title compound. LRMS: 246.1 (M+1).

Method D: 1-{4-Methyl-3-[methyl-(7H-pyrrolo[2,3-d]pyrimidin-4-yl)-amino]-piperidin-1-yl}-ethanone To a stirred solution of the product from Method C (0.03 grams, 0.114 mmol) dissolved in 5 mL of 10:1 dichloromethane/pyridine was added (0.018 grams, 0.228 mmol) of acetylchloride and the resulting mixture stirred at room temperature for 18 hours. The reaction mixture was then partitioned between dichloromethane and saturated sodium bicarbonate ($NaHCO_3$). The organic layer was washed again with saturated $NaHCO_3$, dried over sodium sulfate and concentrated to dryness in vacuo. The residue was purified by preparative thin layer chromatography (PTLC) (silica; 4% methanol in dichloromethane) affording 0.005 mg (15%) of the title compound as a colorless oil. LRMS: 288.1 (M+1).

Method E: Synthesis of 3-1({3R,4R)-4-Methyl-3-[methyl-(7H-pyrrolo[2,3-d]pyrimidin-4-yl)-amino]-piperidin-1-yl}-3-oxo-propionitrile (CP0690550)

The title compound 3-{(3R,4R)-4-Methyl-3-[methyl-(7H-pyrrolo[2,3-d]pyrimidin-4-yl)-amino]-piperidin-1-yl}-3-oxo-propionitrile (CP0690550) was prepared using routine modification of the Methods A-D described above.

Method F: Preparation of 3-{(3R,4R)-4-Methyl-3-[methyl-(7H-pyrrolo[2,3-d]pyrimidin-4-yl)-amino]-piperidin-1-yl}-3-oxo-propionitrile citrate salt The citrate salt was prepared using methods described in WO2007/012953. To a clean, dry, nitrogen-purged 500 ml reactor were charged merthyl-4(-methyl-piperidin-3-yl)-7H-pyrrolo[2,3-d]pyrimidin-4-yl)amine (25.0 g, 0.102 mol) and methylene chloride (250 ml). The mixture was stirred at room temperature for a minimum of 2.5 hours. To a clean, dry, nitrogen-purged 1 L reactor were charged cyanoacetic acid (18.2 g, 0.214 mol), methylene chloride (375 ml), and triethyl amine (30.1 ml, 0.214 mol). The mixture was cooled to −15-5.0° C. over one hour and trimethylacetyl chloride (25.6 ml, 0.204 mol) was added at a rate to maintain the temperature below 0° C. The reaction was held for a minimum of 2.5 hours, then the solution of the amine was added at a rate that maintained the temperature below 0° C. After stirring for 1 hour, the mixture was warmed to room temperature and 1M sodium hydroxide (125 ml) was added. The organic layer was washed with water (125 ml). The methylene chloride solution was displaced with acetone until a volume of 500 ml and a temperature of 55-65° C. had been achieved. Water (75 ml) was charged to the mixture while maintaining the temperature at 55-65° C. A solution of citric acid (20.76 g, 0.107 mol) in water (25.0) was charged and the mixture was cooled to room temperature. The reactor was stirred for a minimum of 5 hours and then the resulting solids were isolated by filtration and washed with acetone (2×75 ml), which was sent to the filter. The salt was charged into a clean, dry, nitrogen-purged 1 L reactor with 2B ethanol (190 ml) and water (190 ml). The slurry was heated to 75-85° C. for a minimum of 4 hours. The mixture was cooled to 20-30° C. and stirred for an additional 4 hours. The solids were isolated by filtration and washed with 2B ethanol (190 ml). After drying in a vacuum oven at 50° C. with a slight nitrogen bleed, 34.6 g (67:3%) of the title compound were isolated.

$^1$H NMR (500 MHz, $d_6$-DMSO): δ 8.14 (s, 1H, 7.11 (d, J=3.6 Hz, 1H), 6.57 (d, J=3.6 Hz, 1H), 4.96 (q, J=6.0 Hz, 1H), 4.00-3.90 (m, 2H), 3.80 (m, 2H), 3.51 (m, 1H), 3.32 (s, 3H), 2.80 (Ab$_q$, J=15.6 Hz, 2H), 2.71 (Abq, J=15.6 Hz, 2H), 2.52-2.50 (m, qH), 2.45-2.41 (m, 1H), 1.81 (m, 1H), 1.69-1.65 (m, 1H), 1.04 (d, J=6.9 Hz, 3H).

Method G: Preparation of free base 3-{(3R,4R)-4-Methyl-3-[methyl-(7H-pyrrolo[2,3-d]pyrimidin-4-yl)-amino]-piperidin-1-yl}-3-oxo-propionitrile The 3-{(3R,4R)-4-Methyl-3-[methyl-(7H-pyrrolo[2,3-d]pyrimidin-4-yl)-amino]-piperidin-1-yl}-3-oxo-propionitrile citrate salt, as prepared in Method F above, was treated with 1M sodium hydroxide in dichloromethane to afford the corresponding free base. The free base was then crystallized from methanol and water to furnish the crystal form of the free base.

Example 2

Pharmaceutical Formulations

Example 2a

Formulations

Table 2 below illustrates various pharmaceutical formulations comprising the inhibitor CP0690550.

TABLE 2

| Formulation code | Formulation Description |
| --- | --- |
| Formulation 1 | 50 mM pH 7.4 phosphate buffer, 0.05% Tween 80, 0.5% NaCl |
| Formulation 2 | 50 mM pH 7.4 Phosphate buffer, 0.36% HPMC, 0.2% Glycerin, 1% PEG400, 0.35% NaCl |
| Formulation 3 | 5 mM pH 7.4 phosphate buffer, 0.36% HPMC, 0.2% Glyerin, 1% PEG400, 5% Cremophor ELP, 4.3% Mannitol |
| Formulation 4 | 10 mM pH 5.8 citrate buffer, 4.5% Mannitol |
| Formulation 5 | 10 mM pH 5.8 citrate buffer, 4.2% Mannitol, 0.36% HPMC, 0.2% Glycerin |
| Formulation 6 | 0.3% tyloxapol (surfactant, nonionic), 0.5% Carbopol974P (polymeric stabilizer, anionic), 2.25% D-mannitol, pH6.5 phosphate buffer at 50 mM concentration, 230 mOsm/kg |
| Formulation 7 | 0.3% tyloxapol (surfactant, nonionic), 0.1% Carbopol974P (polymeric stabilizer, anionic), 2.25% D-mannitol, pH6.5 phosphate buffer at 50 mM concentration, 230 mOsm/kg |

Example 2b

Preparation

Each of the above formulations 1 through 5 were prepared comprising the Jak3 inhibitor CP0690550 in three dosage amounts: 0.001%, 0.003% and 0.01% w/w. Formulation 5 was also prepared with the Jak3 inhibitor CP9690550 in the amount of 0.005% w/w (see FIG. 8). Formulations 6 and 7 were prepared comprising Jak3 inhibitor in the amount of 0.03% w/w.

The above formulations were prepared by adding the required amount of the tonicity agent (hypromellose, or mannitol where present) to a flask, heating to about to about 50° C. in half the final volume of buffer (phosphate or citrate buffer as indicated). After heating the batch quantities of inhibitor CP690550, the additional excipients (glycerin, polyethylene glycol 400, where indicated) were weighed and dissolved. The batch quantity of the Jak3 inhibitor free base as a stock solution was measured and added. Purified water was added to q.s. to 100%. The mixture was stirred for five minutes to homogenize and then filtered through a sterilizing filter membrane into a sterile recipient. If necessary, pH was adjusted by admixture of 1.0 NaOH.

Formulations 6 and 7 represent ophthalmic compositions in which higher amounts of the inhibitor CP690550 are present (0.03% w/w). In addition to a tonicity agent and buffer, such higher concentrate formulations will also include a surfactant and optionally a stabilizing polymer. Preferred surfactants of the invention include TritonX114 and tyloxapol. Preferred stabilizing polymers include the carbomer 974p.

Preparation of Formulations 6 and 7 were prepared by dispersing the carbomer first in the surfactant containing buffer at 10× of their final concentration (e.g. 3% tyloxapol in 50 mM phosphate buffer at pH6.5 with 2.5% D-mannitol and 5% Carbomer 974p). The Jak3 inhibitor CP690550 was dispersed in the preconcentrate also at 10× of its final concentration. The mixture was then homogenized, with final formulation being obtained by 10× dilution of filtered preconcentrate in a matching buffer.

Example 3

Effect of Selective Jak3 Inhibitor on Tear Production MRL/Ipr (Dry Eye) Mice

To study the level of tear production over time, 10 MRL/Ipr mice and 5 of the age-matched C57 Black/6 control mice at 8 weeks of age were purchased from Jackson Laboratory (Bar Harbor, Me., USA). The mouse strain MRL/Ipr has a mutation which predisposes it to dry eye similar to Sjogren's Syndrome.

Figure 1:
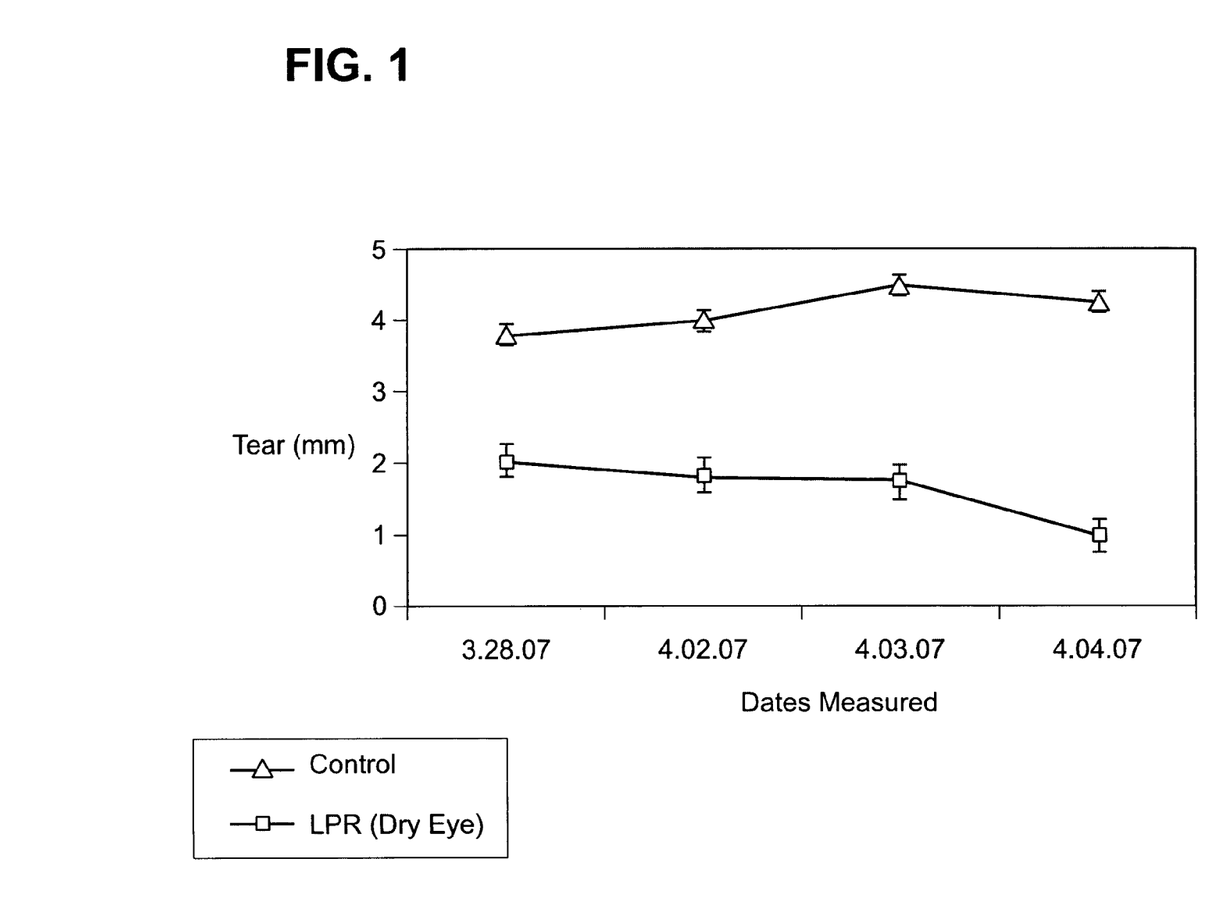
FIG. 1 shows tear production of the MRL/Ipr mouse ("dry eye mouse") versus the control C57 mouse as discussed in Example 1 below.

Baseline tear volume was established by measuring of tear volume 4 times over one week to establish that dry eye occurred in MRL/Ipr mice versus C57 mice. Tear production was measured with cotton thread (Quick Zone®) held with forceps and applied to the ocular surface at the lateral canthus for 15 to 30 seconds. Wetting of the thread was measured in millimeters. Tear production measurements of MRL/Ipr mice versus C57control mice are shown in FIG. 1.

Animals (5-10 mice/group) were treated with 20 of either vehicle (phosphate buffered saline, PBS, containing 0.05% Tween 80) or 0.1% (w/w) CP-690550 twice a day for two weeks. C57 mice also received vehicle. Tear volume was measured on days 2, 3, and 6. The effect of CP-690550 on tear production in MRL/Ipr Mice is shown in FIG. 2.

Figure 2:
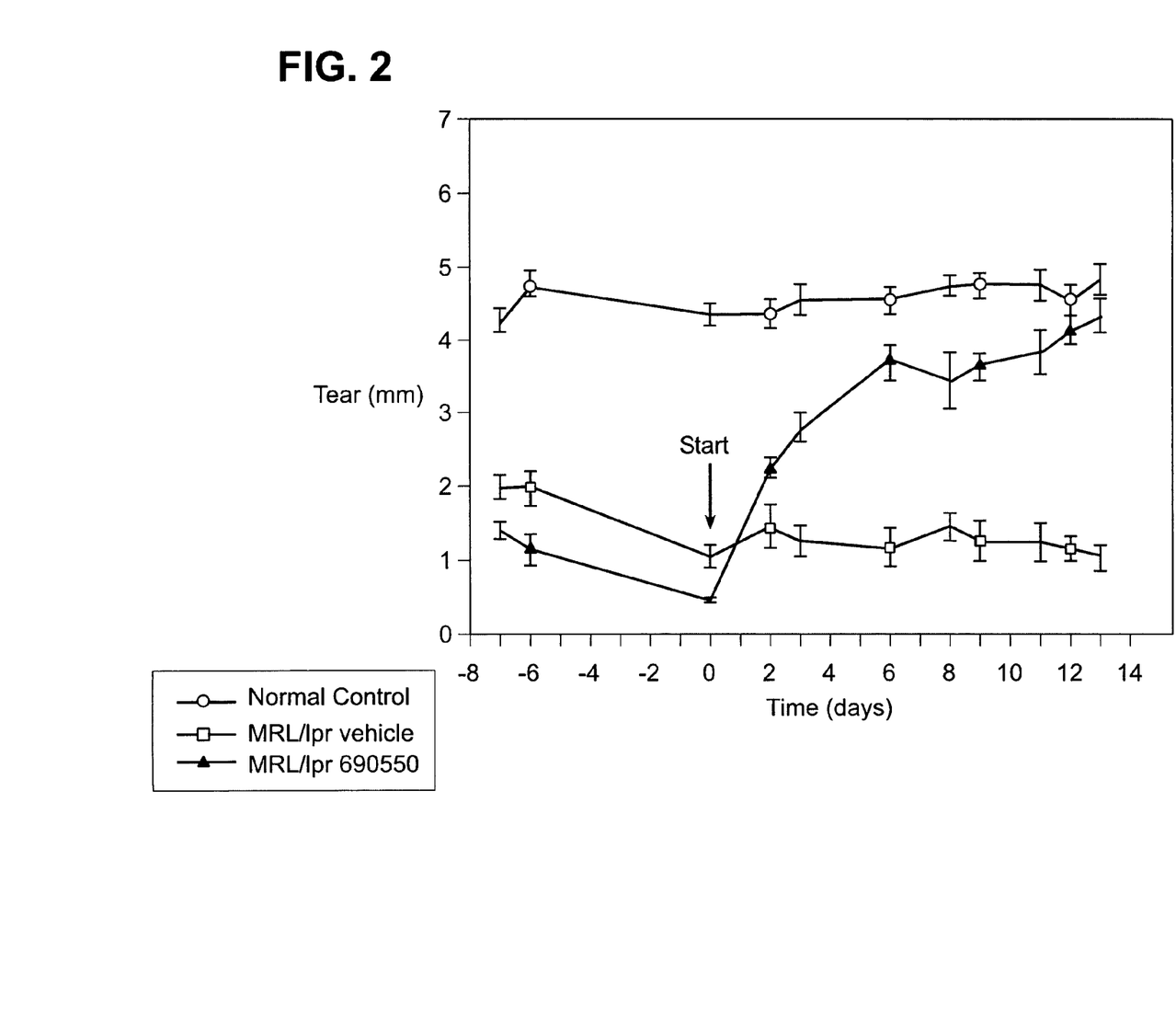
FIG. 2 shows tear production of the dry eye mouse versus the C57 mouse, as when administered with the selective Jak3 inhibitor, 3-{(3R,4R)-4-Methyl-3-[methyl-(7H-pyrrolo[2,3-d]pyrimidin-4-yl)-amino]-piperidin-1-yl}-3-oxo-propionitrile (CP0690550).

As shown in FIG. 2, CP0690550 was able to significantly increase tear production volume within the first 2 days of application. Notably, CP690550 increased tear production volume by over 100% over initial tear production of the dry eye mice within the first 2 days of application.

Example 4

Comparative Data Comparing CP-690550 to Restasis®

Tear measurement was done using phenol red impregnated thread (Quick Zone®) and baseline measurement was performed before each drug application. Drugs or vehicles were applied at 2 µl, two times a day.

Vehicle-treated normal C57black/6 and MRL/Ipr dry eye mice were used as normal control and dry eye control, respectively. The vehicle for CP690550 was phosphate buffered saline, PBS, containing 0.05% Tween 80.

The experiment to compare efficacy of CP-690550 and Restasis® was done using Restasis® (cyclosporine 0.05%) and CP-690550 at 0.01% applied twice a day for 30 days. Control animals included normal C57Black/6 mice, and MRL/Ipr mice, treated with PBS vehicle and MRL/Ipr mice treated with Refresh Endura® (vehicle for Restasis) (5-10 mice/group). Comparative tear production of CP-690550 and Restasis® is shown in FIG. 3.

Figure 3:
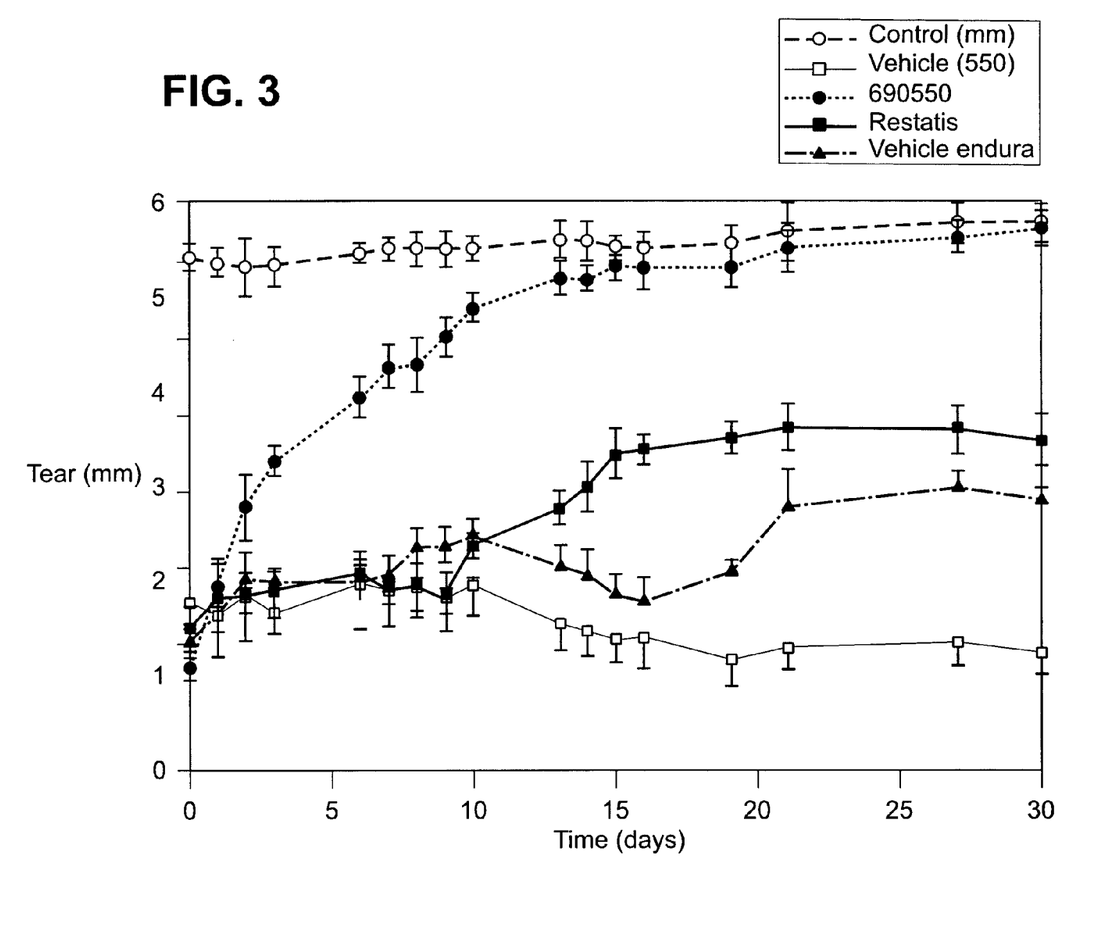
FIG. 3 shows tear production of the Jak3 inhibitor CP0690550 as compared to the leading dry eye therapeutic Restasis®.

As shown in FIG. 3, CP690550 had a much faster response rate as compared to Restasis® and showed a significant improvement in the volume of tear production over Restasis®.

Figure 4:
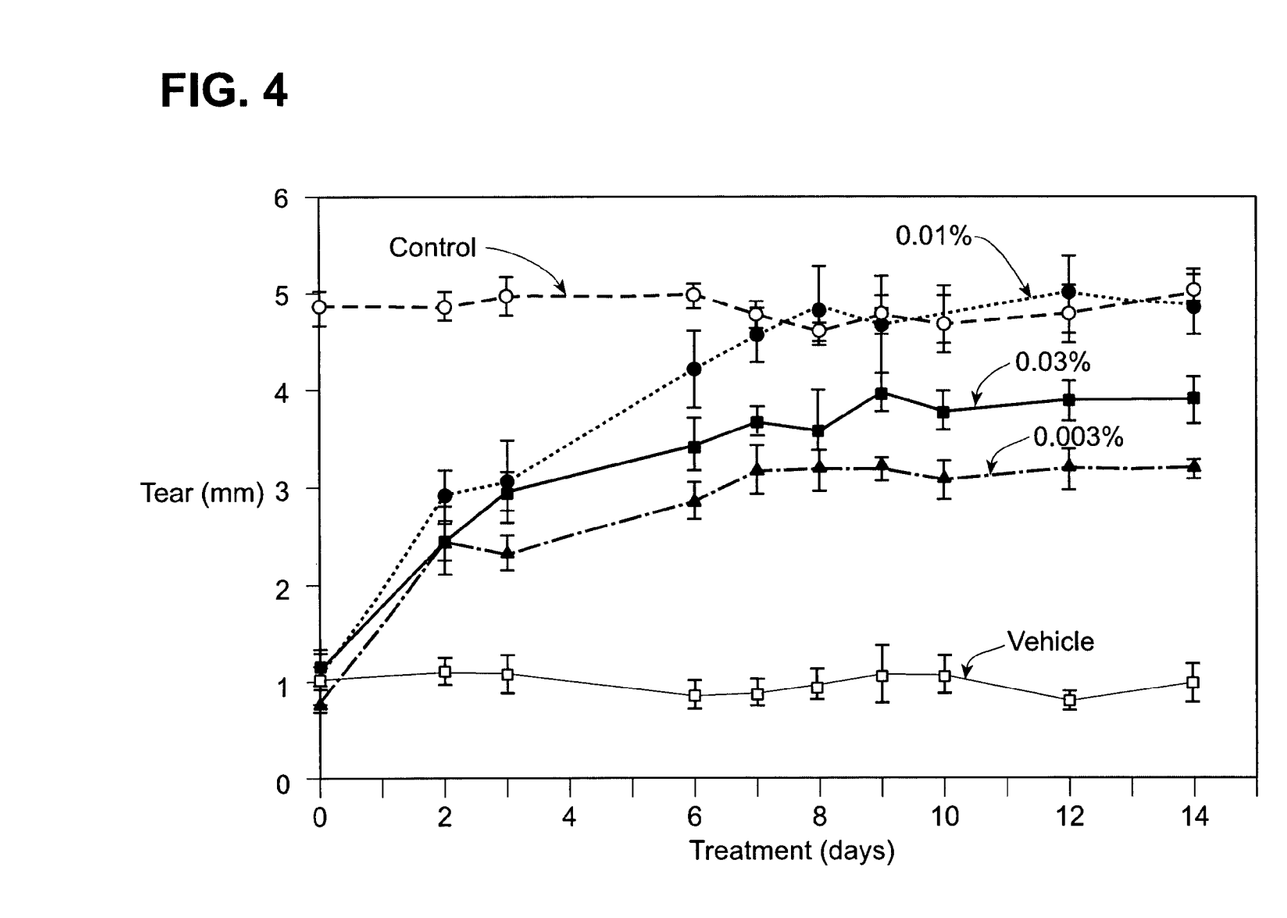
FIG. 4 shows the dose response effects of CP690550 at 0.003%, 0.01%, and 0.03% (w/w) in Formulation 1 vehicle as compared to normal and dry eye controls.

Moreover, both FIGS. 3 and 4 indicate that administration of CP690550 ultimately increased tear production volume to a level comparable to that of normal tear production (within 5 to 10% of tear production by "normal" C57mice).

Example 5

Dose Response Rates of CP690550 in MRL/Ipr Mice

As with Example 4 above, vehicle-treated normal C57black/6 and MRL/Ipr dry eye mice (5-10 mice/group) were used as normal control and dry eye control, respectively. The vehicles for CP690550 were Formulations 1, 3 and 4 as indicated in Example 2 above. The Jak3 inhibitor CP690550 was applied at 0.003% (w/w), 01% (w/w) and 0.03% (w/w), as calculated for free base concentration. Treatment for Formulation 1 was carried for two weeks, at 2 µl, twice a day. Treatment for Formulations 3 and 4 were carried for 2 weeks, at 1 µl, once a day.

Figure 5:
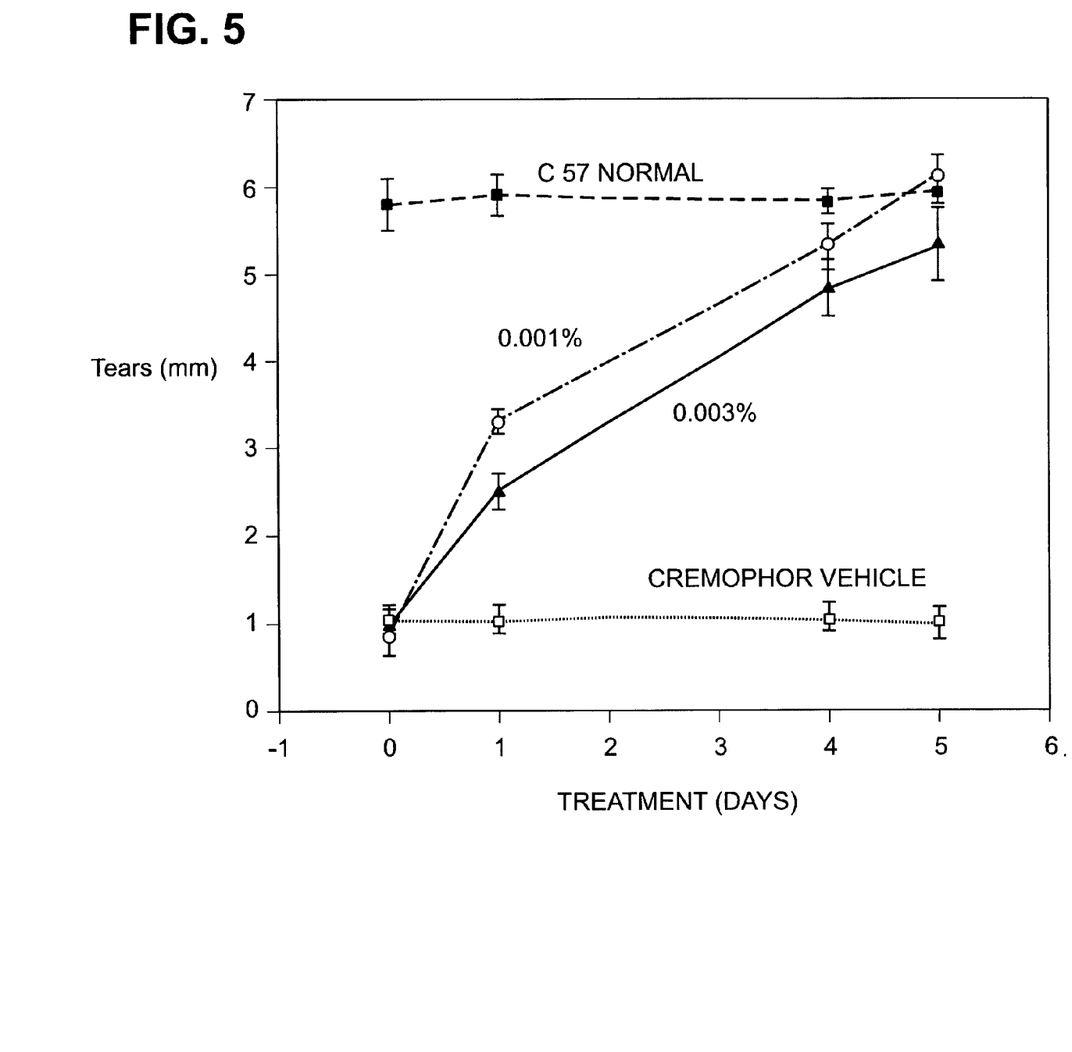
FIG. 5 shows the dose response effects of CP690550 at 0.001% and 0.003% (w/w) in Formulation 3 vehicle, as compared to normal and dry eye controls.
Figure 6:
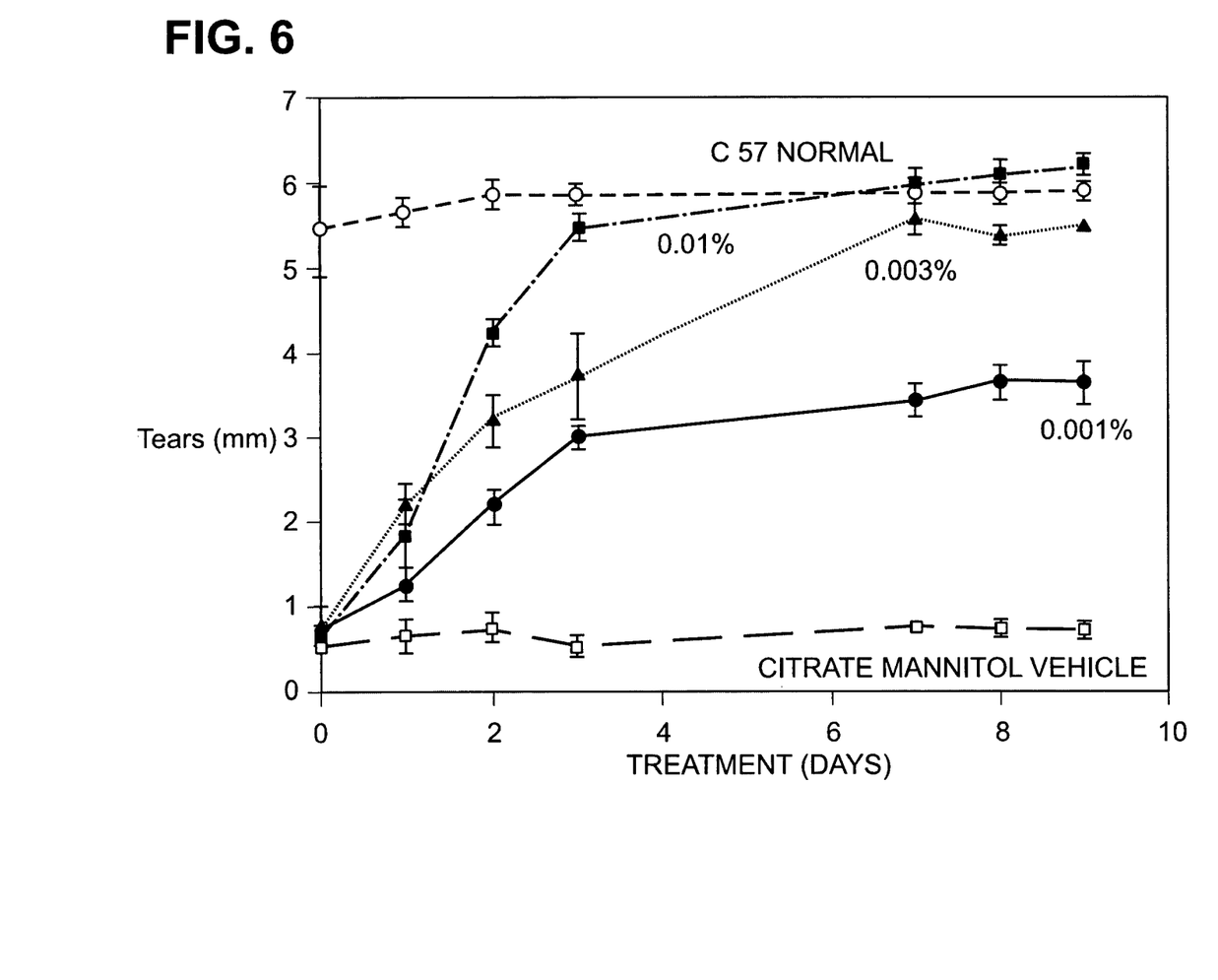
FIG. 6 shows the dose response effects of CP690550 at 0.001%, 0.003% and 0.01% (w/w) in Formulation 4 vehicle, as compared to normal and dry eye controls.

FIG. 4 illustrates that within 8 days, administration of CP690550 in Formulation 1 vehicle at 0.01% (w/w) twice a day increased tear production to a level comparable to that of normal tear production (within 5 to 10% of tear production by C57 normal mice). Similarly, FIGS. 5 and 6 illustrate dose response rates of CP690550 in Formulations 3 and 4 vehicle. In all comparisons, significant improvement in tear production was shown at 2 days after treatment.

Example 6

Induced Dry Eye Mouse Model

An injection was prepared comprising 2.5 mg/ml scopolamine (sigma) in injectable saline (1-1.5 ml per animal). In normal C57 mice (200-250) ul of scopolamine was injected four times every 2.5 hrs in alternating hind quarters. The mice were placed in special cages (with holes in front and back) and placed in a hood. Fans were placed in front of each cage, and turned on for 16 hours over night for five days.

Measurements were taken daily. At the end of 5 days, all animals were considered dry-induced.

Figure 7:
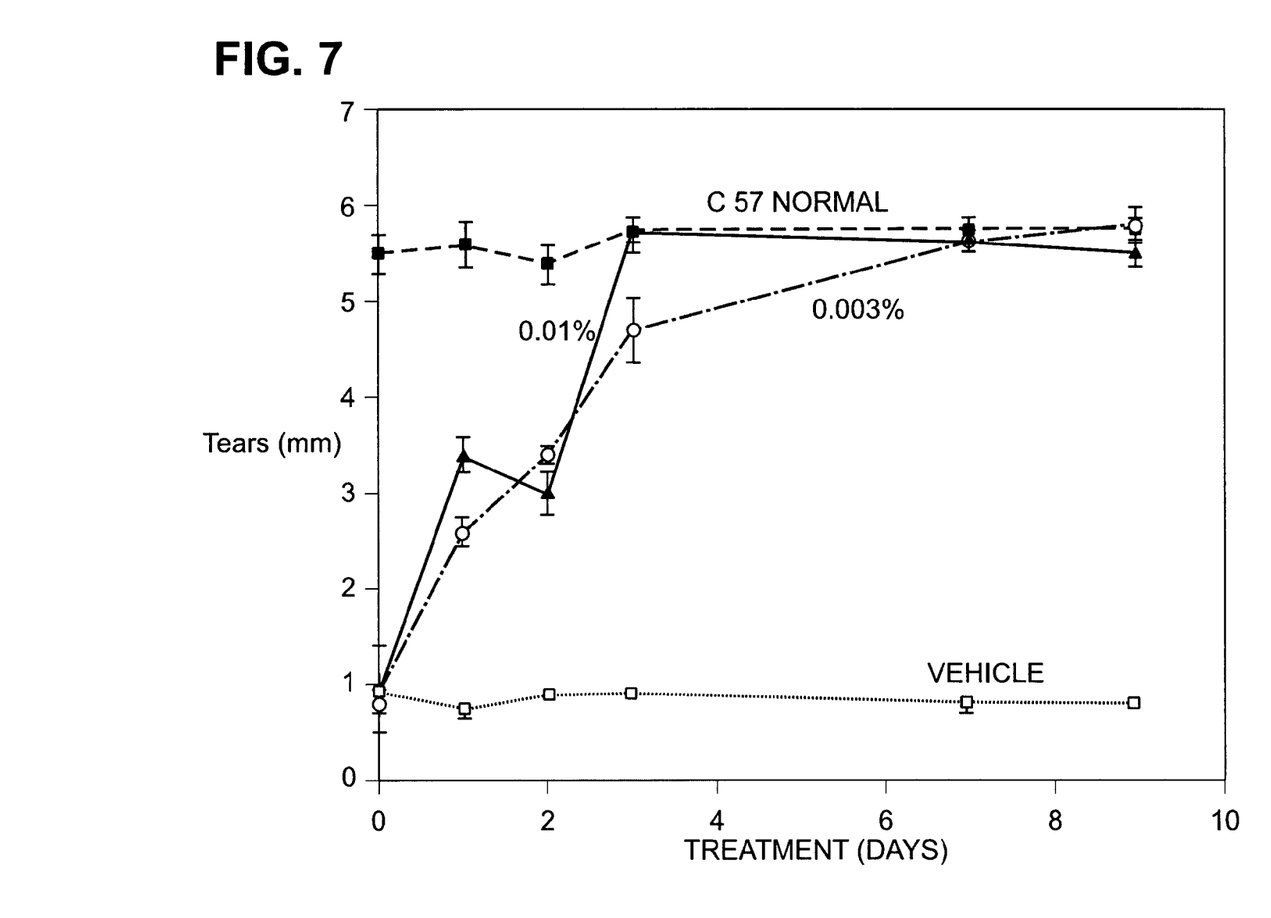
FIG. 7 shows the dose response effects of CP690550 at 0.003% and 0.01% (w/w) in Formulation 3 vehicle in an induced dry eye mouse model, as compared to normal eye and placebo vehicle controls.
Figure 8:
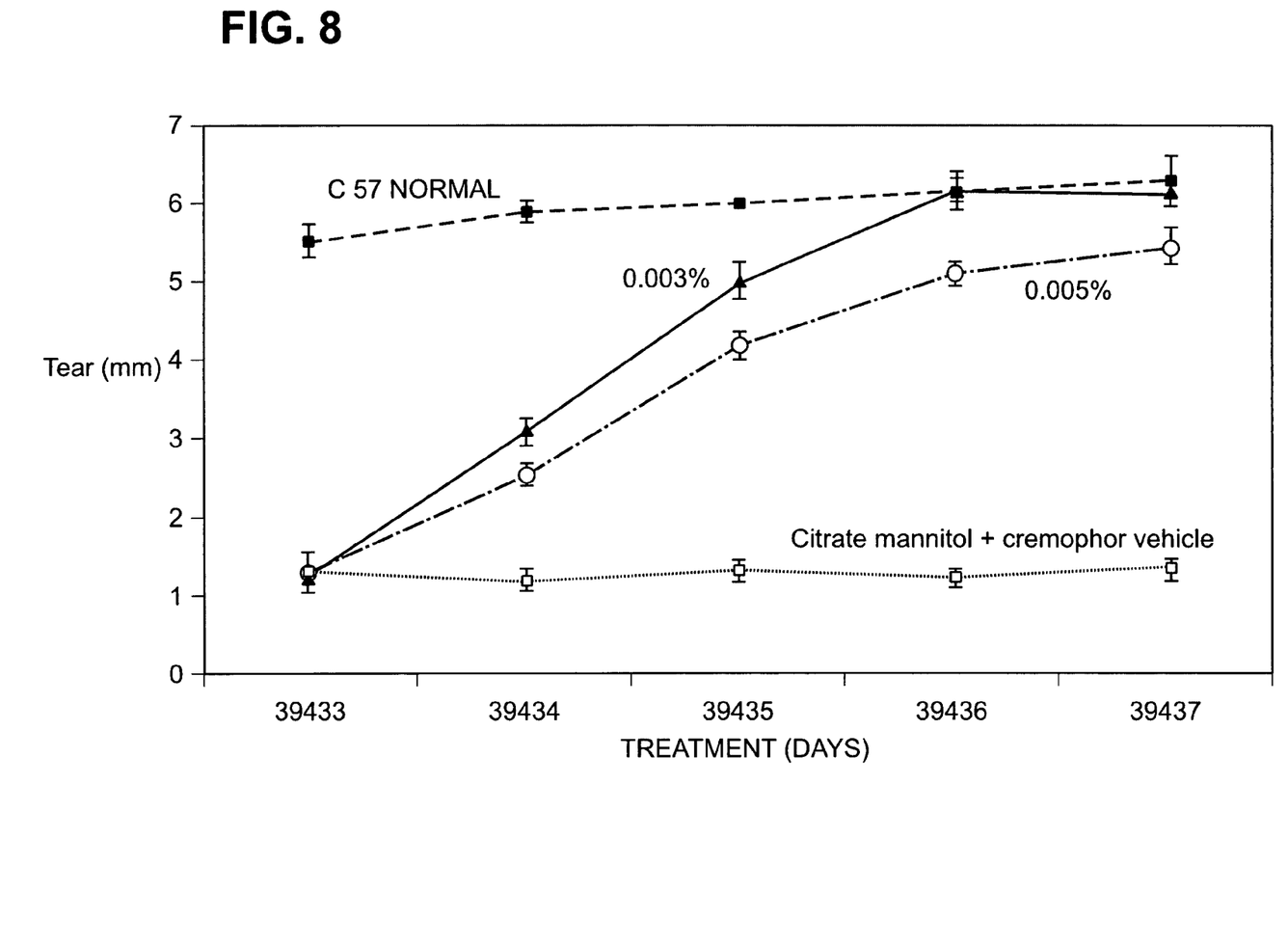
FIG. 8 shows the dose response effects of CP690550 at 0.003% and 0.005% (w/w) in Formulation 5 vehicle in an induced dry eye mouse model, as compared to normal eye and placebo vehicle controls.

As with Examples 4 and 5 above, animals were treated with drug or vehicle at 1 µl, once a day for 2 weeks. Vehicle-treated C57 black/6 and the dry-induced mice (5-10 mice/group) were treated with Formulations 3 and 5 as prepared in Example 2 above. FIGS. 7 and 8 illustrate that a significant increase in tear production was shown at 2 days of treatment. After 4 days of treatment, formulations comprising 0.01% (w/w) of CP0690550 inhibitor in Formulation 3 and 0.003% of CP690550 inhibitor in Formulation 5 approximated normal tear production values.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of an inflammation-linked ocular disorder selected from the group consisting of glaucoma, uveitis, diabetic retinopathy, age-related macular degeneration and dry eye, comprising administering topically to the eye of a mammal in need thereof a topical ophthalmic composition comprising a pharmaceutically effective amount of a Janus kinase-3 ("Jak3") inhibitor having the structure or a pharmaceutically effective salt thereof.

2. The method of claim 1, wherein the method significantly increases tear production volume as compared to untreated tear production volume within two days.

3. The method of claim 1, wherein the method increases tear production volume by at least 50% over initial tear production within two days.

4. The method of claim 1, wherein the method increases tear production volume to a level comparable to that of normal tear production.

5. The method of claim 1, wherein the Jak3 inhibitor is administered at most twice a day (BID).

6. The method of claim 1, wherein the Jak3 inhibitor is administered daily (QD).

7. A method for restoration of normal tear production in a mammal comprising, administering topically to the eye of a mammal in need thereof a topical ophthalmic composition comprising a pharmaceutically effective amount of a Janus kinase-3 ("Jak3") inhibitor having the structure 3-{(3R,4R)-4-Methyl-3-[methyl-(7H-pyrrolo[2,3-d]pyrimidin-4-yl)-amino]-piperidin-1-yl}-3-oxo-propionitrile.

8. The method of claim 1, wherein the pharmaceutically effective amount of Jak3 inhibitor is 0.0001 to less than 0.1% (w/w).

9. The method of claim 1, wherein the pharmaceutically effective amount of Jak3 inhibitor is 0.003 to 0.03% (w/w).

10. The method of claim 1, wherein the pharmaceutically effective amount of Jak3 inhibitor is 0.01 to 0.03% (w/w).

* * * * *